United States Patent [19]

Yamamura et al.

[11] 4,191,778

[45] Mar. 4, 1980

[54] AQUEOUS IMMUNOREGULATORY AGENT

[75] Inventors: Yuichi Yamamura, Takarazuka; Ichiro Azuma, Suita; Kazuhisa Sugimura, Toyonaka; Hiroshi Morimoto, Nishinomiya; Isuke Imada, Izumi; Masazumi Watanabe, Kawanishi, all of Japan

[73] Assignee: Takeda Chemical Industries, Ltd., Osaka, Japan

[21] Appl. No.: 766,505

[22] Filed: Feb. 7, 1977

[30] Foreign Application Priority Data

Feb. 10, 1976 [JP] Japan ................................ 51-13584

[51] Int. Cl.² .......................................... H61K 31/19
[52] U.S. Cl. ............................................ 424/317
[58] Field of Search .......................................... 424/317

[56] References Cited

U.S. PATENT DOCUMENTS 3,957,836 5/1976 Morimoto et al. .................. 424/317

FOREIGN PATENT DOCUMENTS 10574 4/1975 Japan .......................... 424/317

OTHER PUBLICATIONS

Imada et al., Immunology, 43, pp. 898–906 (1972).

*Primary Examiner*—Jerome D. Goldberg
*Attorney, Agent, or Firm*—Wenderoth, Lind & Ponack

[57] ABSTRACT

The aqueous preparation such as an aqueous solution, a water-in-oil emulsion, in which a water-soluble salt of the quinonyl acid derivative of the formula:

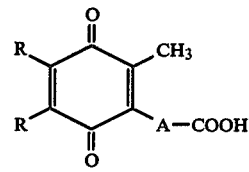

[wherein each R is a lower alkoxy group having 1 to 4 carbon atoms or the two R's, taken together, represent a group of —CH=CH—CH=CH—; —A—COOH means

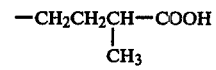

when both R's are lower alkoxy groups, or —(CH$_2$)$_n$COOH (wherein n is an integer from 1 to 8) when two R's, taken together, represent a group of —CH=CH—CH=CH—] is dissolved in aqueous phase, shows an excellent immunoregulatory activity in animals including human being.

8 Claims, No Drawings

AQUEOUS IMMUNOREGULATORY AGENT

This invention relates to an immunoregulatory agent. More particularly, the invention relates to an aqueous immunoregulatory preparation containing a water-soluble salt of a quinonyl acid derivative of the general formula (I):

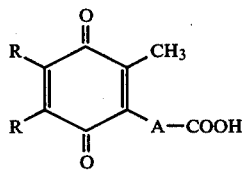

[wherein each R is a lower alkoxy group having 1 to 4 carbon atoms or the two R's, taken together, represent a group of —CH=CH—CH=CH—; —A—COOH means

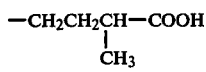

when both R's are lower alkoxy groups, or —(CH$_2$)$_n$COOH (wherein n is an integer from 1 to 8) when the two R's, taken together, represent a group of —CH=CH—CH=CH—].

The principal and essential object of the present invention is to provide an agent showing an immunoregulatory activity in animals including human beings.

The term "immunoregulatory activity" as used in the context of this invention means activities to enhance the immune response of a human being or an animal when the response has been depressed, to counteract or arrest a suppressive action upon the production of humoral antibody when used in conjunction with a drug having the suppressive action as its side effect and to display an immunosuppressive action when said response is in hypersensitized condition.

The conditions of depressed immune response are exemplified by those attributable to immunodeficiency syndrome due to aging and other causes, and the drug having a suppressive action as its side effect upon the production of antibodies in sera is exemplified by certain antibiotics and carcinostatic agents. As cases of hypersensitized immune response, there may be mentioned ordinary autoimmune diseases and allergic diseases.

The aqueous immunoregulatory agent according to this invention not only arrests depressions in the titers of natural antibodies in immunodeficiency syndrome and thereby helps guard against infections but, when used as an adjunct to adrenocortical steroid therapies which are commonly used for treatment of autoimmune diseases, inhibits depressions in immune responses and thereby enhances therapeutic effects, in addition to its remedial action upon allergic diseases such as bronchial asthma. Therefore, the immunoregulatory agent of this invention is of value, for example, as an anti-infective agent, or as a drug for the treatment of bronchial asthma.

The general formula (I) given hereinbefore may be written in two ways:

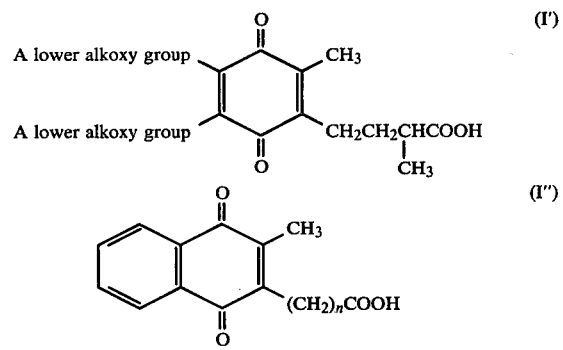

(In the above formulas, n is an integer from 1 to 8).

Referring to the general formula (I), the lower alkoxy group having 1 to 4 carbon atoms designated by R may be exemplified by methoxy, ethoxy, n-propoxy, iso-propoxy and n-butoxy. Among them methoxy is particularly desirable. As to the integer n which ranges from 1 to 8, preferred numbers are 4 to 8.

Some of quinonyl acid derivatives (I) are known compounds and, as for routes of production, the method described in the specification of Japanese Patent Publication No. 10574/1975 and that described in U.S. Pat. No. 2,398,418 may be mentioned by way of example. New species among quinonyl acid derivatives (I) can also be synthesized generally in the manner known as above.

As the water-soluble salts of quinonyl acid derivatives (I) employable according to this invention, there may be mentioned alkali metal salts (e.g. sodium salt, potassium salt, etc.), alkaline earth metal salts (e.g. magnesium salt, calcium salt etc.), amine salts (e.g. ammonium salt, trimethylamine salt, triethylamine salt, etc.) and so on. Particularly desirable are alkali metal salts, the sodium salt being the most suitable.

The aqueous immunoregulatory agent of this invention may assume any form, provided that its principal medicament salt of quinonyl acid derivative occurs as dissolved in water. Thus, aqueous preparations for injection and oral administration may be mentioned, for instance. As specific examples of such dosage forms there may be mentioned an aqueous solution (e.g. a solution of the medicament in pure water or in physiological saline), a water-in-oil emulsion with the principal medicament quinonyl acid derivative (I) occurring in the aqueous phase and an aqueous dilution of such a water-in-oil emulsion. A water-in-oil emulsion is particularly desirable. Where an immunostimulant effect is desired, such as aqueous agent may further contain suitable antigens which may for example be water-soluble protein antigens (e.g. bacterial α-amylase), particulate glycoprotein or polysaccharide antigens (e.g. sheep erythrocyte) and so forth. Like ordinary aqueous preparations, the present aqueous agent may further contain a stabilizer, buffer, preservative and other additives which are preferably highly water-soluble and such that they will, as they are, not affect the immune responses of animals including human beings. As examples of said preservative, there may be mentioned benzyl alcohols, phenols, p-oxybenzoic acids and so forth.

As the oils that may be used in the preparation of said water-in-oil emulsion and its aqueous dilution, there may be mentioned mineral oils (n-paraffin, n-hexadecane, mixtures thereof, etc.), vegetable oils (sesame oil, peanut oil, olive oil, etc.) and animal oils (squalene, etc.). Preferred are the oils which will be decomposed with considerable difficulty in vivo. the ratio of oil to water in such a water-in-oil preparation may be one to 3 volumes of water to each volume of oil, the preferred ratio being 1:1. An amulsifier is normally employed in the preparation of such water-in-oil emulsion, the amount of such emulsifier depending upon the types of amounts of the oil, water, quinonyl acid derivative (I) employed and other substances which may be added and, particularly, upon the relative amounts of water and oil. Normally, preferable content of an emulsifier in the said water-in-oil emulsion is 0.1 to 20% by volume, preferably 1 to 20% by volume. Where approximately equal volume of water and oil are employed, the emulsifier is added so as to make its proportion in the final preparation to be of 1 to 15% by volume, preferably 1 to 10% by volume. The emulsifier may be any emulsifying substance which is not detrimental to living tissues at or below the above upper limit. Thus, for example, lanolin, polysorbate 80, mannitol monooleate, polyoxyethylene-vegetable oil derivatives (e.g. polyoxyethylene castor oil derivative), etc. may be mentioned. The amount of water used in the preparation of said aqueous dilution of water-in-oil emulsion is in the range of 1 to 500 volume parts based upon the volume of said water-in-oil emulsion, the range of 100 to 400 times the volume of the latter being preferred.

The aforementioned various aqueous products may be prepared by procedures known per se for the production of aqueous pharmaceutical preparations. Thus, for example, said aqueous solution may be normally prepared by dissolving a water-soluble salt of quinonyl acid derivative (I) in water (preferably physiological saline); and water-in-oil emulsion may be normally prepared by admixing an aqueous solution of salt of quinonyl acid derivative (I) (which may further contain antigens) with a mixture of oil and an emulsifier; and said aqueous dilution of water-in-oil emulsion may be prepared by admixing such a water-in-oil emulsion with water (preferably physiological saline). Such aqueous products may, if necessary, be sterilized in a conventional manner for oral or parenteral use.

The content of the water-soluble salt of quinonyl acid derivative (I) in such an aqueous product is dictated by the required dose and, normally, it is preferred that the salt be contained in a proportion of 0.1 to 10% as the free acid.

The dosage of the aqueous product according to this invention may be selected with reference to the type of water-soluble salt, symptoms, dosage form and other factors. Where it is used as an aqueous solution or as a water-in-oil emulsion, the product is normally administered at a level of 5 to 500 mg. daily (by injecting) or 10 to 1000 mg. daily (by the oral route) per adult human as the free quinonyl acid derivative (I). In the case of small animals such as mice, while it depends upon their body weights, the preferred dose levels are normally 100 $\mu$g. to 5 mg. (parenterally) or 200 $\mu$g. to 10 mg. (orally) per diem.

Throughout the specification, milligram(s), microgram(s) and milliliter(s) are abbreviated as "mg.", "$\mu$g." and "ml.", respectively.

EXAMPLE 1

Bacterial α-amylase (1 mg.) as an antigen and 2,3-dimethoxy-5-methyl-6-(3'-carboxybutyl)-1,4-benzoquinone sodium salt (5 mg.) are dissolved in physiological saline (a 0.9% aqueous solution of sodium chloride, 1 ml.) and the resultant solution is added dropwise with vigorous stirring to a mixture (1 ml.) of paraffin oil-mannitol monooleate (17:3) to obtain a water-in-oil emulsion.

EXAMPLE 2

The procedure of Example 1 is repeated except that 2-methyl-3-(4'-carboxybutyl)-1,4-naphthoquinone sodium salt (5 mg.) is used in lieu of the benzoquinone derivative mentioned in Example 1 to obtain in water-in-oil emulsion.

EXAMPLE 3

Under warming, 2,3-dimethoxy-5-methyl-6-(3'-carboxybutyl)-1,4-benzoquinone (5 mg.) is dissolved in a 3.7% solution of sodium bicarbonate is physiological saline (0.05 ml.; this solution contains about 1.2 moles of sodium bicarbonate to each mole of said benzoquinone derivative), followed by the addition of physiological saline to make a total of 1 ml. The resultant dilution is treated with paraffin oil in the same manner as Example 1 to obtain a water-in-oil emulsion.

EXAMPLE 4

The procedure of Example 3 is repeated except that 2-methyl-3-(4'-carboxybutyl)-1,4-naphthoquinone (5 mg.) is used in lieu of the benzoquinone derivative mentioned in Example 3 to obtain a water-in-oil emulsion.

EXAMPLE 5

Under warming, 2,3-dimethoxy-5-methyl-6-(3'-carboxybutyl)-1,4-benzoquinone is dissolved in a 3.7% solution of sodium bicarbonate in physiological saline (0.05 ml.; this solution contains about 1.2 moles of sodium bicarbonate based on said benzoquinone derivative), followed by the addition of physiological saline to make 1 ml. The resultant solution is used as the aqueous product of the invention.

REFERENCE EXAMPLE 1

The procedure of Example 3 is repeated except that 2,3-dimethoxy-5-methyl-6-(2'-carboxyethyl)-1,4-benzoquinone is used in lieu of the benzoquinone derivative used in Example 3 to prepare a water-in-oil emulsion.

REFERENCE EXAMPLE 2

The procedure of Example 3 is repeated except that 2-methyl-3-(5'-carboxy-3'-methyl-2'-pentenyl)-1,4-naphthoquinone is used in lieu of the benzoquinone derivative used in Example 3 to prepare a water-in-oil emulsion.

REFERENCE EXAMPLE 3

The procedure of Example 5 is repeated except that 2,3,5-trimethyl-6-(5'-carboxy-3'-methylpentyl)-1,4-benzoquinone is employed in lieu of the benzoquinone derivative used in Example 5 to obtain an aqueous solution.

REFERENCE EXAMPLE 4

In a 17:3 mixture (1 ml.) of paraffin oil and mannitol monooleate is dissolved 2,3-dimethoxy-5-methyl-6-(3'-carboxybutyl)-1,4-benzoquinone (5 mg.) and, then, a solution of bacterial α-amylase (1 mg.) in physiological saline (1 ml.) is added dropwise with vigorous stirring to obtain a water-in-oil emulsion.

REFERENCE EXAMPLE 5

The procedure of Reference Example 4 is repeated except that ubiquinone-7 is used in lieu of the benzoquinone derivative used in Reference Example 4 to obtain a water-in-oil emulsion.

REFERENCE EXAMPLE 6

The procedure of Example 3 is repeated except that no benzoquinone derivative is employed to prepare a water-in-oil emulsion.

EXPERIMENTAL DATA 1

The spleen of a mouse (C 57 BL/6J) was minced and suspended in Eagles' medium and passed through a metal mesh to prepare a cell suspension which was centrifuged and rinsed. By the method of Marbrook (Lancet Vol.II for 1967, page 1279), the washed spleen cells ($2 \times 10^7$) and $4 \times 10^6$ sheep erythrocyte were suspended in PRMI-1640 medium containing 10% of bovine fetal calf serum. The suspension was put in the internal tube of the Marbrook tissue culture apparatus, with 12 ml. of the same medium being put in the outer tube. In test groups, a solution of the test material in physiological saline was put in the internal tube to incubate. As test materials, the aqueous solution (A) according to Example 5, the aqueous solutions (B) according to Reference Example 3 and the aqueous solution (C) without the present aqueous product were employed. The cultures were placed in a humidified incubator at 37° C. with a constant flow of gas (10% $CO_2$ in air). After incubation for 4 days, the cells in the internal tube were harvested. Antibody-producing cells were counted by a version of Jerne's method [Pierce, Journal of Experimental Medicine 130, 345 (1969)]. As shown in Table I, it was found that the immunoregulatory effect of the aqueous product according to this invention is very pronounced and that the production of antibody is enhanced in the group (I) with a low immune response and suppressed in the groups (II,III) with high immune responses.

Table I

| Test material | Dose, µg./mouse (as the amount of principal medicament) | No. of plaque-forming cells in spleen | | |
|---|---|---|---|---|
| | | Group I | Group II | Group III |
| A | 10 | 694 | — | 950 |
| A | 100 | 800 | 750 | — |
| B | 10 | — | — | 4500 |
| B | 100 | — | 2800 | — |
| C | — | 544 | 3705 | 6600 |

EXPERIMENTAL DATA 2

The water-in-oil emulsion of 2,3-dimethoxy-5-methyl-6-(3'-carboxybutyl)-1,4-benzoquinone sodium salt (a) obtained in Example 3, the water-in-oil emulsion of 2,3-dimethoxy-5-methyl-6-(2'-carboxyethyl)-1,4-benzoquinone sodium salt (c) according to Reference Example 1, the water-in-oil emulsion containing 2,3-dimethoxy-5-methyl-6-(3'-carboxybutyl)-1,4-benzoquinone in the oil phase (e) according to Reference Example 4, the water-in-oil emulsion containing ubiquinone-7 in the oil phase (f) according to Reference Example 5 and the control oil emulsion (g) were each administered to mice [(C 57 BL/6J $\times$ DBA/2)F$_1$; briefly BDF$_1$ hereinafter] at a rate of 0.2 ml. by the intraperitoneal route. After 42 days, blood samples were taken from the retroorbital venous plexus and the titers of anti-bacterial α-amylase antibody in sera were determined by the method of Okada et al. [Journal of Biochemistry 54, 477 (1963)]. The results are shown in Table II. It will be seen that the titer of antibody in sera of the group treated with the immunoregulatory agent of this invention is several times higher than the titers for the control and other treated groups.

Table II

| | Effects on antibody production in sera | |
|---|---|---|
| Test material | Dose, µg./mouse (as the amount of principal medicament) | Anti-bacterial α-amylase antibody titer in sera* |
| (a) | 500 | 393 |
| (c) | 500 | 270 |
| (e) | 500 | 60 or less |
| (f) | 500 | 93 |
| (g) | 0 | 60 |

*Antibody titer to bacterial α-amylase was determined by the capacity of antiserum to inhibit the amylase activity of the antigen.

EXPERIMENTAL DATA 3

The solution (0.2 ml.) of 2,3-dimethoxy-5-methyl-6-(3'-carboxybutyl-1,4-benzoquinone sodium salt (1 mg.) in physiological saline according to Example 5 or physiological saline (0.2 ml.) alone was intraperitoneally injected into BDF$_1$ mice two days and one day before and on the very day of primary immunization. At one hour after the injection of the very day mentioned above, a solution (0.5 ml.) of bacterial α-amylase as antigen (1 mg.) in physiological saline was intraperitoneally injected (primary immunization). Then, 35 days later, a secondary immunization was accomplished with a solution (0.5 ml.) of bacterial α-amylase (200 µg.) in physiological saline. Fourteen days after the secondary immunization, the titer of anti-bacterial α-amylase antibody in sera was determined. As will be seen from Table III, the titer of antibody increased about 4-fold for the group dosed with the aqueous immunoregulatory agent.

Table III

| Effects of the immunoreguratory agent of the invention upon the production of antibody in sera | |
|---|---|
| Group | Titer of antibody in sera |
| Dosed with physiological saline | 47 |
| Dosed with the aqueous immunoregulator of the invention | 197 |

EXPERIMENTAL DATA 4

BDF$_1$ mice were intraperitoneally dosed with hydrocortisone (1.5 mg.). After 2 days, sheep erythrocyte ($2 \times 10^8$) as an antigen were intraperitoneally administered. Five days later, the spleens were separated and the antibody-forming cell populations (plaque-forming cells; briefly PFC hereinafter) were counted by the plaque method of Jerne [Science 140, 405(1963)]. The result showed that the number of PFC had suppressed as compared with the normal control group. On the other hand, in the groups dosed intravenously with the aqueous immunoregulatory agent of Example 5 simultaneously or 2 or 3 days after the administration of hydrocortisone, the number of PFC as determined by the same immunization and determination procedure were comparable to the number for the normal control group as shown in Table IV.

Table IV
Effects of the immunoregulatory agent of this invention upon the immune response of mice dosed with hydrocortisone

| Group* | No. of PFC per $10^6$ spleen cells | %** |
|---|---|---|
| Control (untreated) | 579 ± 39 | 100 |
| Hydrocortisone | 393 ± 89 | 68 |
| Hydrocortisone + Aq. immunoregulatory agent of this invention | | |
| (Simultaneous)*** | 734 ± 71 | 127 |
| (2 days later) | 562 ± 126 | 97 |
| (3 days later) | 692 ± 44 | 120 |

*Each group consisted of 5 mice.
**The percentage of PFC in each treated group, with PFC population for the untreated control group being taken as 100.
***Times after the administration of hydrocortisone.

EXPERIMENTAL DATA 5

BDF$_1$ mice were intraperitoneally dosed with 0.2 ml. of the water-in-oil emulsion (a) of 2,3-dimethoxy-5-methyl-6-(3′-carboxybutyl)-1,4-benzoquinone sodium salt according to Example 3, the water-in-oil emulsion (b) of 2-methyl-3-(4′-carboxybutyl)-1,4-naphthoquinone sodium salt according to Example 4, the water-in-oil emulsion (c) of 2,3-dimethoxy-5-methyl-6-(2′-carboxyethyl)-1,4-benzoquinone sodium salt according to Reference Example 1, the water-in-oil emulsion (d) of 2-methyl-3-(5′-carboxy-3′-methyl-2′-pentenyl)-1,4-naphthoquinone sodium salt according to Reference Example 2 or the control water-in-oil emulsion (g) according to Reference Example 6. After 12 and 42 days, blood samples were taken from the retroorbital venous plexus and the titer of anti-bacterial α-amylase antibody in each serum was determined by a method similar to the method of Kishimoto et al [International Archives of Allergy and Applied Immunology 34, 544 (1963)]. As will be seen from Table V, the titer of antibody in sera for the group dosed with the immunoregulatory agent of this invention was more than twice higher than the titers for the control and other treated groups.

Table V
Effect of the immunoreguratory agent upon the production of antibody in sera

| Test material | Dose, μg/mouse (as the amount of principal medicament) | Anti-bacterial α-amylase antibody titer in sera* | |
|---|---|---|---|
| | | 12 days after immunization | 42 days after immunization |
| (a) | 500 | 4096 | 16384 |
| (b) | 500 | 4096 | 8192 |
| (c) | 500 | 2048 | — |
| (d) | 500 | 2048 | — |
| (g) | 0 | 1024 | 1024 |

*The titers were determined by a passive hemagglutination.

What is claimed is:

1. An aqueous immunoregulatory agent containing a physiologically acceptable water-soluble alkali metal or amine salt of a quinonyl acid derivative of the formula

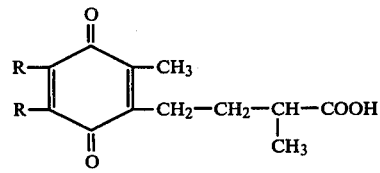

wherein each R represents lower alkoxy, said water-soluble salt being present in a proportion of 0.1 to 10% as the free acid, and an aqueous carrier.

2. An aqueous immunoregulatory agent as claimed in claim 1, wherein said water-soluble salt of quinonyl acid derivative is its alkali metal salt.

3. An aqueous immunoregulatory agent as claimed in claim 2, wherein said alkali metal salt is the sodium salt.

4. An aqueous immunoregulatory agent as claimed in claim 1, wherein each R represents a lower alkoxy group having 1 to 4 carbon atoms.

5. An aqueous immunoregulatory agent as claimed in claim 4, wherein each R is methoxy.

6. An aqueous immunoregulatory agent as claimed in claim 1, wherein said salt of quinonyl acid derivative by way of principal medicament is present in the form of an aqueous solution.

7. An aqueous immunoregulatory agent as claimed in claim 1, wherein said salt of quinonyl acid derivative by way of principal medicament is present in the form of a water-in-oil emulsion.

8. An aqueous immunoregulatory agent as claimed in claim 7, wherein said water-in-soil emulsion has been diluted with water.